(12) United States Patent
Bourne et al.

(10) Patent No.: US 7,294,110 B2
(45) Date of Patent: Nov. 13, 2007

(54) MEDICAL INSTRUMENTS

(75) Inventors: George Bourne, Southboro, MA (US); David Cooke, Groveland, MA (US)

(73) Assignee: Boston Scientific SciMed Inc., Maple Grove, MN (US)

(*) Notice: Subject to any disclaimer, the term of this patent is extended or adjusted under 35 U.S.C. 154(b) by 327 days.

(21) Appl. No.: 10/300,511

(22) Filed: Nov. 20, 2002

(65) Prior Publication Data

US 2004/0097831 A1 May 20, 2004

(51) Int. Cl.
*A61B 10/00* (2006.01)
(52) U.S. Cl. ..................................... 600/564
(58) Field of Classification Search ............... 600/564, 600/567, 562, 570, 108, 131, 135, 139, 158; 606/153, 170, 171; 403/267; 30/343, 526; 74/557, 551.9; 73/1.82; 264/1.7; 16/408, 16/430, 902, 422, DIG. 12, 114.1, 421; 473/203; 401/6, 88; 15/145
See application file for complete search history.

(56) References Cited

U.S. PATENT DOCUMENTS

| | | | |
|---|---|---|---|
| 1,908,834 A | 5/1933 | Engberg et al. | |
| 3,813,729 A * | 6/1974 | Szabo et al. | 16/408 |
| 4,147,348 A | 4/1979 | Lee | |
| 4,147,443 A | 4/1979 | Skobel | |
| 4,246,444 A | 1/1981 | Mason | |
| 4,284,275 A | 8/1981 | Fletcher | |
| 4,476,742 A | 10/1984 | Midgley | |
| 4,696,842 A | 9/1987 | Doubt | |
| 4,932,800 A | 6/1990 | Lin et al. | |
| 4,934,024 A | 6/1990 | Sexton, I | |
| 4,976,269 A * | 12/1990 | Mehl | 600/567 |
| 5,155,878 A | 10/1992 | Dellis | |
| 5,183,054 A * | 2/1993 | Burkholder et al. | 600/567 |
| 5,333,603 A * | 8/1994 | Schuman | 600/108 |
| 5,348,360 A | 9/1994 | Mencarelli et al. | |
| 5,353,474 A | 10/1994 | Good et al. | |
| 5,390,572 A | 2/1995 | Gakhar et al. | |
| 5,404,267 A | 4/1995 | Silva et al. | |
| 5,446,941 A | 9/1995 | Kelsay | |
| 5,499,422 A | 3/1996 | Lavazoli | |
| 5,511,445 A | 4/1996 | Hildebrandt | |
| 5,542,462 A | 8/1996 | Elsenheimer et al. | |
| 5,554,098 A | 9/1996 | Yabe et al. | |
| 5,690,113 A | 11/1997 | Silwa, Jr. et al. | |
| 5,797,165 A | 8/1998 | Armbrust | |
| 5,810,733 A | 9/1998 | Van Creveld et al. | |
| 5,860,190 A | 1/1999 | Cano | |

(Continued)

FOREIGN PATENT DOCUMENTS

EP    0 159 453    4/1984

OTHER PUBLICATIONS

MatWeb spec sheet for Versaflex, http://www.matweb.com/search/SpecificMaterialPrint.asp?bassnum=PGLSCV07.*

(Continued)

*Primary Examiner*—Max F. Hindenburg
*Assistant Examiner*—Brian Szmal
(74) *Attorney, Agent, or Firm*—Fish & Richardson P.C.

(57) ABSTRACT

A medical instrument includes a gripping section having a first portion having a first composition, and a second portion over a selected portion of the first portion. The second portion has a second composition different than the first composition.

29 Claims, 5 Drawing Sheets

U.S. PATENT DOCUMENTS

| | | | |
|---|---|---|---|
| 5,876,134 A * | 3/1999 | Tseng et al. | 401/6 |
| 5,897,503 A | 4/1999 | Lyon et al. | |
| 5,928,154 A | 7/1999 | Silber et al. | |
| D426,448 S | 6/2000 | Ferrari et al. | |
| 6,070,329 A | 6/2000 | Gibbs | |
| 6,128,808 A | 10/2000 | Jansson et al. | |
| 6,148,483 A | 11/2000 | DeGraff | |
| RE37,190 E | 5/2001 | Stowell et al. | |
| 6,237,192 B1 | 5/2001 | Garrison et al. | |
| 6,270,134 B1 | 8/2001 | Lin | |
| 6,485,211 B1 * | 11/2002 | Leo et al. | 401/6 |
| 2002/0016603 A1 | 2/2002 | Wells | |
| 2002/0148277 A1 * | 10/2002 | Umeda | 73/1.82 |

OTHER PUBLICATIONS

PCT International Search Report, dated Apr. 29, 2004.

* cited by examiner

MEDICAL INSTRUMENTS

TECHNICAL FIELD

The invention relates to medical instruments.

BACKGROUND

A biopsy needle instrument can be used to obtain a tissue specimen for microscopic examination, e.g., to determine malignancy, while preferably subjecting the patient to the least trauma. In some embodiments, the instrument has of a long, thin probe, called a stylet, within a close-fitting hollow needle, called a cannula. The stylet has a notch into which tissue can prolapse when the stylet enters the tissue.

During use, a firing device first projects the stylet into tissue, followed immediately by the cannula. As the cannula slides over the stylet, the cannula severs tissue from the surrounding mass that has prolapsed into the notch of the stylet, and captures the prolapsed tissue as a specimen within the notch. The instrument can then be withdrawn and the piece of tissue removed from the stylet.

SUMMARY

The invention relates to medical instruments.

In one aspect, the invention features a medical instrument having a handle or a gripping section including two or more compositions, for example, polymers with different hardness and/or resiliency. The compositions can be selected and arranged to make the handle relatively comfortable and/or relatively easy to grip, for example, without slipping when the handle is wet. For some instruments, such as biopsy needle instruments, the compositions can be selected and constructed to reduce, e.g., absorb, mechanical shock and/or sound generated during use. As a result, performance of the instruments is enhanced.

In another aspect, the invention features a medical instrument including a gripping section having a first portion having a first composition, and a second portion irremovably over a selected portion of the first portion. The second portion includes a second composition different than the first composition.

In another aspect, the invention features a needle biopsy instrument including a handle having a first portion including a first composition, and a second portion over a selected portion of the first portion. The second portion includes a second composition different than the first composition.

Embodiments of the aspects of the invention may include one or more of the following features. The first composition is harder than the second composition. The second portion defines one or more flexible ridges. The gripping section has a recess, and the second portion is over the recess. The gripping section further includes an adhesive between the first portion and the second portion. The second portion interlocks with the first portion. The selected portion contacts a user during use. The second portion substantially covers the first portion.

The first composition and/or the second composition can include a polymer. For example, the first composition can include polycarbonate or acrylonitrile-butadiene-styrene. The second composition can include a urethane.

The gripping section can be generally linear or a pistol-like.

The instrument can be, for example, a needle biopsy instrument, an endoscope or an ultrasound probe.

In another aspect, the invention features a medical instrument including a gripping section having a first portion having a first composition, and a second portion irremovably attached to the first portion. The second portion includes a second composition different than the first composition.

In another aspect, the invention features a method of using the medical instruments described herein in a medical procedure, e.g., a biopsy, an endoscopic procedure, or an ultrasound procedure.

Embodiments of the aspects of the invention may include one or more of the features described above or below, in any combination.

As used herein, "irremovable" means that a component cannot be easily removed; for example, a user cannot remove the component without using tools or excessive force.

Other aspects, features, and advantages of the invention will be apparent from the description of the preferred embodiments thereof and from the claims.

DETAILED DESCRIPTION

Figure 1A:
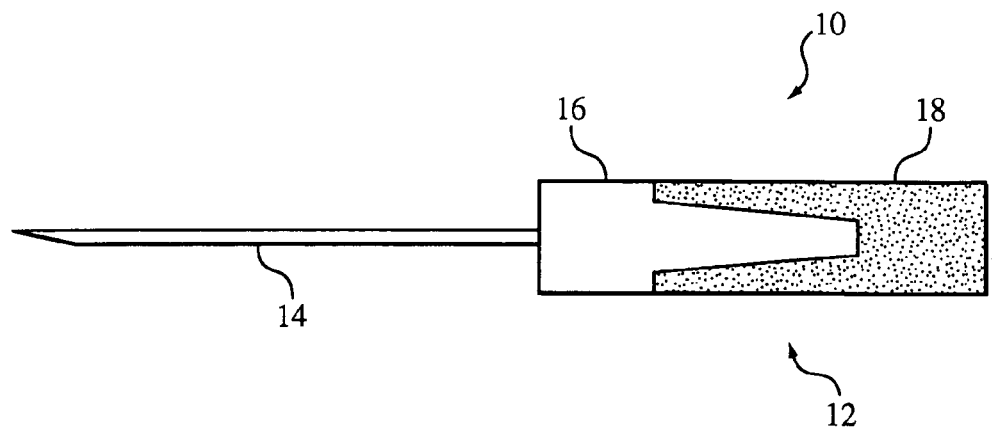
FIG. 1A is a schematic drawing of an embodiment of a medical instrument.
Figure 1B:
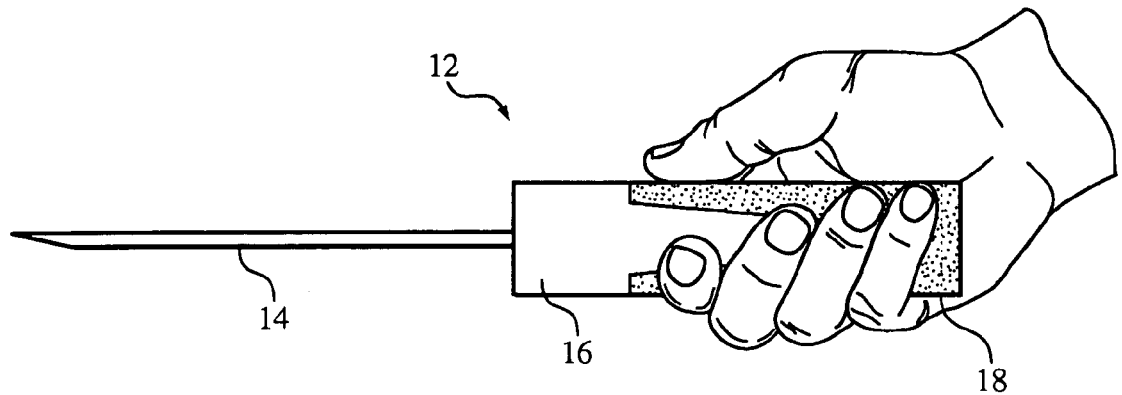
FIG. 1B is an illustration of the instrument of FIG. 1A as held by a user.

Referring to FIGS. 1A and 1B, a medical instrument 10, as shown, a needle biopsy instrument, includes a generally linear handle or a gripping section 12 and a cannula 14 extending from the handle. Handle 12 includes a base portion 16 formed of relatively rigid or semi-rigid material(s), and one or more resilient portions 18 (here, one) formed of a relatively soft, resilient material. The combination of base portion 16 and resilient portion 18 provides a gripping section with good tactile qualities, such as those that make handle 16 easy to grasp securely, e.g., when handle 12 is wet with blood or other fluids.

Base portion 16 is generally configured as a core section of handle 12. For example, for a needle biopsy instrument, base portion 16 can be configured as two half-shells that house the components of the instrument. An example of a needle biopsy instrument having a generally linear housing for a handle is described in Chin et al., U.S. Pat. No. 5,195,533, and Bates, U.S. Pat. No. 4,958,625. Suitable materials for base portion 16 include rigid or semi-rigid moldable plastics having sufficient strength and rigidity to serve as a structural support. Examples of materials include polyacetals, polycarbonates, acrylonitrile butadiene styrene (ABS), polymethyl methacrylate (PMMA), polyamides such as NYLON 6/6, polyolefins, such as polyethylene and polypropylene, and blends of polymers, such as ABS/polycarbonate. In some embodiments, the base material has a hardness of at least 40 Shore D, e.g. from about 40 to 90 Shore D. Other suitable materials include metals, such as aluminum, and alloys, such as stainless steel. Base portion 16 can be formed of two or more materials.

Resilient portion 18 is formed on one or more selected portions of base portion 16. The selected portions can include those portions of base portion 16 that can be grasped by a user. For example, the selected portions can include portions that are contacted by the user's palm and/or fingers when the user grasps handle 12. The selected portions of base portion 16 can be recessed so that after resilient portion 18 is formed, handle 12 has a smooth, uninterrupted profile. In some embodiments, a user can contact both base portion 16 and resilient portion(s) 18 while using device 10, e.g., to provide a secure and comfortable grip, and to provide a contrast in texture that can enhance the feel of handle 12. Resilient portion 18 can be formed to extend over substantially the entire surface area of handle 12 or a fraction of the surface area. In some embodiments, resilient portion 18 covers greater than or equal to about 10%, 20%, 30%, 40%, 50%, 60%, 70%, 80%, or 90% of the surface area of handle 12; and/or less than or equal to about 100%, 90%, 80%, 70%, 60%, 50%, 40%, 30%, 20%, or 10% of the surface area of the handle.

Suitable materials for resilient portion(s) 18 include resilient materials that are durable enough to withstand use during the lifetime of device 10, e.g., without tearing or abrading, and hard enough to provide a secure-feeling grip, while also being sufficiently soft to provide a comfortable degree of cushioning and good tactile properties during use. In some embodiments, the resilient material has a hardness of less than about 100 Shore A, e.g., from about 20 to 100 Shore A.

Examples of materials for resilient portion(s) 18 include thermoplastic elastomers (TPEs). Suitable TPEs include thermoplastic vulcanates (rubber polyolefin blends), polyetheramides, polyesters, styrene-ethylene-butylene-styrene (SEBS) block copolymers, styrene-butadiene-styrene (SBS) block copolymers, partially or fully hydrogenated styrenebutadiene-styrene block copolymers, styrene-isoprene-styrene (SIS) block copolymers, partially or fully hydrogenated styrene-isoprene-styrene block copolymers, polyurethanes, polyolefin elastomers, polyolefin plastomers, styrenic based polyolefin elastomers, compatible mixtures thereof, and similar thermoplastic elastomers. SEBS, SBS and SIS block copolymers are commercially available from Shell under the tradename KRATON rubber. Other suitable thermoplastic elastomers include, e.g., KRATON rubber-based block copolymers such as DYNAFLEX G2701 and DYNAFLEX G2755 polymers, commercially available from GLS Corp., Cary, Ill. Other suitable resilient materials include the PEBAX® family of polymers (available from ElfAtoChem, Philadelphia, Pa. which can be used pure or as blends), resilient urethanes, silicones, rubbers, and foams. Suitable foams include polyurethane foams, e.g., those prepared from compositions having two components: a foamable, curable polyurethane prepolymer, and an aqueous phase containing a latex and a surfactant. Still other materials are described in U.S. Ser. No. 09/798,749, filed Mar. 2, 2001. The resilient material can include additives, such as plasticizers, fillers or pigments. The additive can be selected to provide the resilient material with a desired surface texture. The resilient material can include open cells or closed cells. A medical device can include two or more resilient portions 18 having different compositions or the same composition. In certain embodiments, each resilient portion 18 can include one or more materials. Any of the resilient materials described above can be used with any of the materials for base portion 16, in any combination.

Handle 12 can be formed by co-molding base portion 16 and resilient portion(s) 18 using conventional co-molding techniques. For example, an injection mold with moving plates can be used, in which case one of the materials is introduced into the mold cavity with the plates in a first position, and the plates are then moved to a second position prior to introduction of the other material. This type of injection molding equipment is well known in the molding field, and utilizes two separate melt barrels to facilitate two different materials being melted into a single mold.

Other methods of forming handle 12 are possible. For example, in some embodiments, resilient portion(s) 18 is attached to base portion 16 with an adhesive, such as a pressure-sensitive adhesive or an epoxy. In other embodiments, base portion 16 includes opening(s) through which resilient material can flow (e.g., during injection molding), and set on both sides of the base portion, thereby mechanically locking the resilient material to the base portion.

After handle 12 is formed, it can be incorporated into device 10, which can be used in a conventional manner.

Figure 2A:
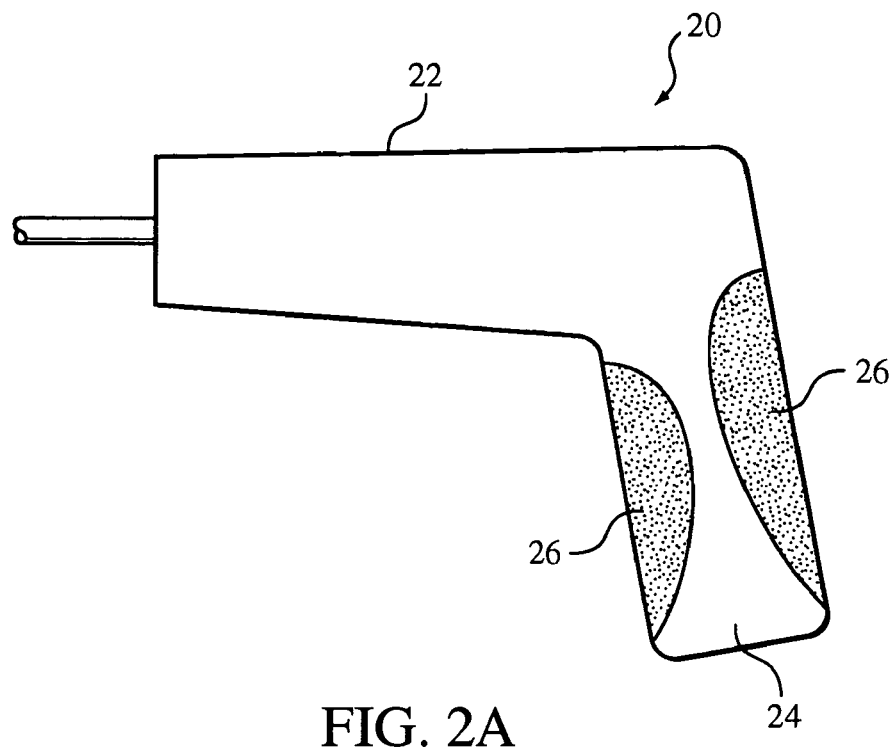
FIG. 2A is a schematic drawing of an embodiment of a handle.
Figure 2B:
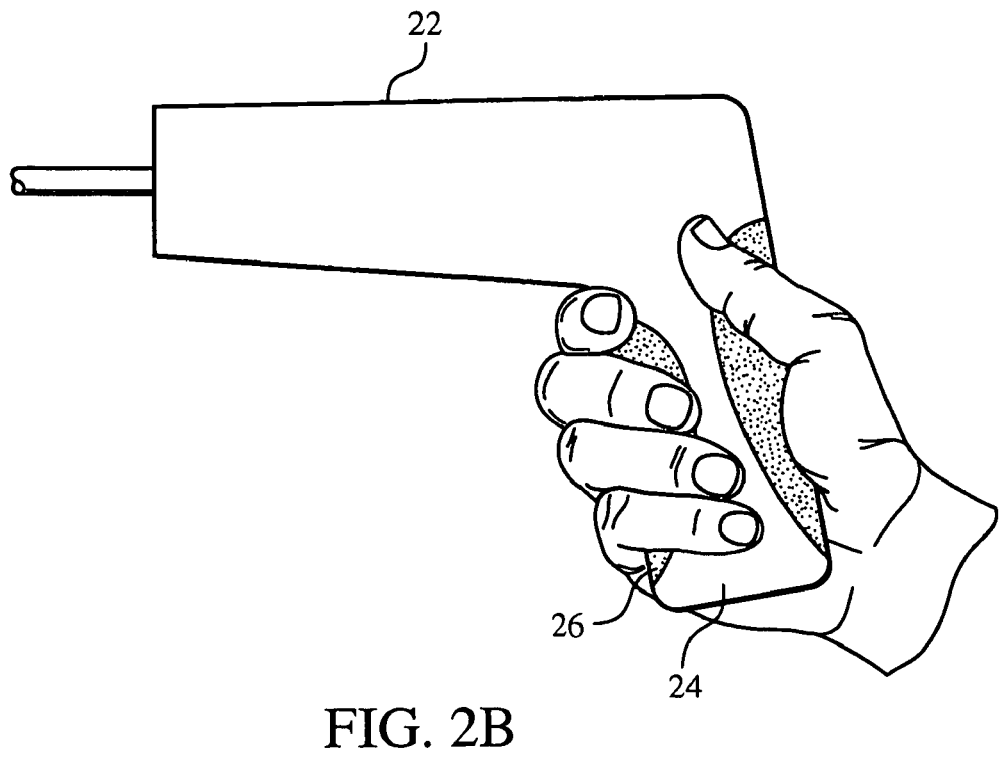
FIG. 2B is an illustration of the handle of FIG. 1A as held by a user.
Figure 3:
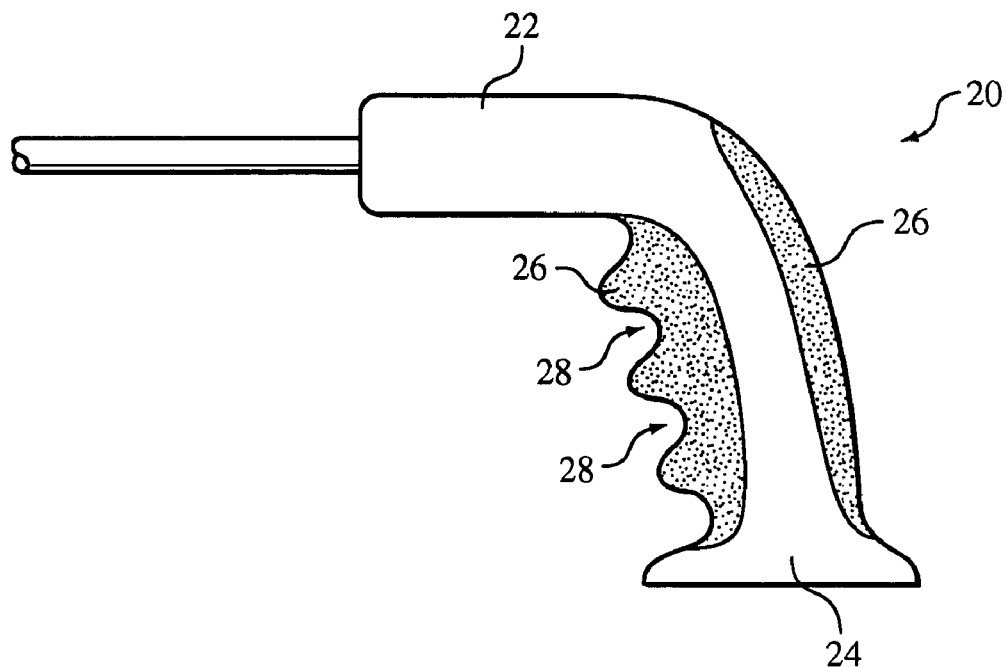
FIG. 3 is a schematic drawing of an embodiment of a handle.

In general, handle 12, base portion 16, and resilient portion(s) 18 can be formed in numerous other configurations. Referring to FIGS. 2A and 2B, a pistol-like handle or grip 20 includes a longitudinal section 22 and a gripping section 24. Sections 22 and 24 can be made of a rigid material as described above for base portion 16. Gripping section 24 includes two resilient portions 26, generally as described above for resilient portion 18. Resilient portions 26 are formed such that they contact a user's palm and fingers during use (FIG. 2B). In other embodiments, referring to FIG. 3, handle 20 includes grooves 28 configured to receive the user's fingers during use, and a resilient portion 26 is formed over the grooves. Grooves 28 can be formed on handle 12. Handle 12 or 20 can be incorporated into a medical device, such as tissue or bone marrow extracting devices described in U.S. Pat. Nos. 6,110,176, and 5,857,982.

Figure 4:
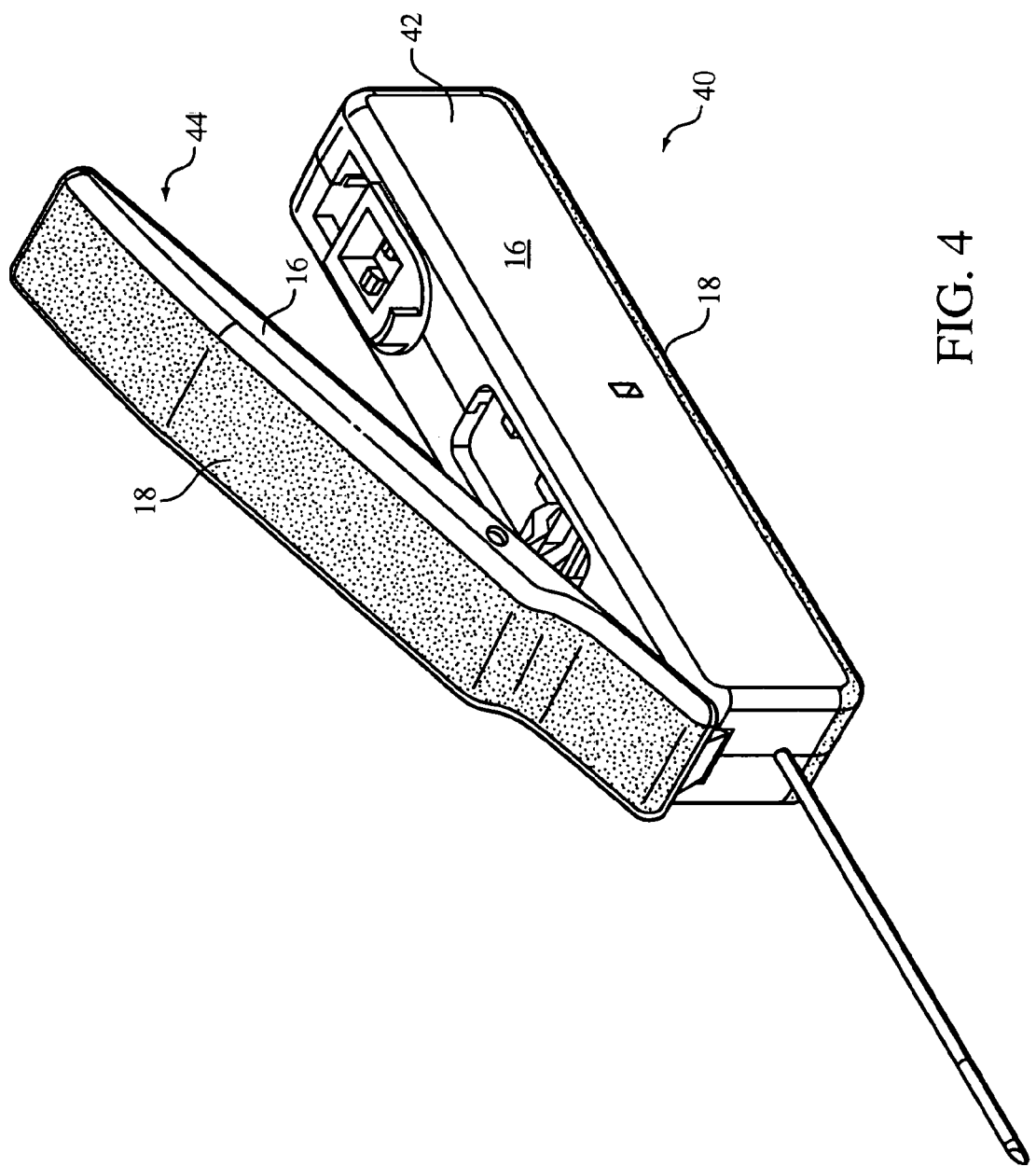
FIG. 4 is a perspective view of an embodiment of a biopsy instrument.
Figure 5:
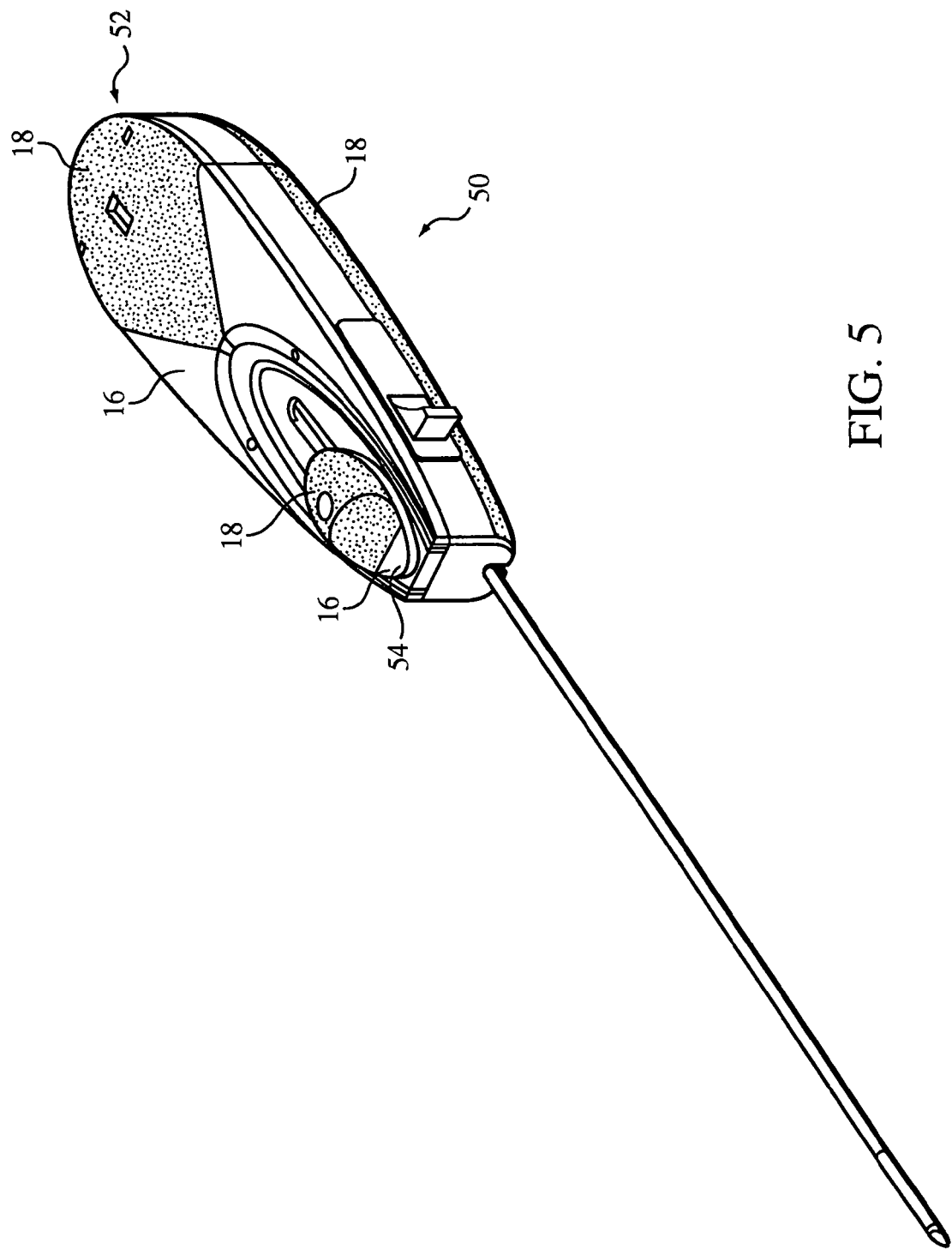
FIG. 5 is a perspective view of an embodiment of a biopsy instrument.

Other configurations of needle biopsy instruments can include body portion 16 and resilient portion(s) 18. FIG. 4 shows an instrument 40 having a housing 42 and a lever 44 for operating the instrument. Housing 42 and lever 44 can be formed as generally described for handle 12 having base portion 16 and resilient portion(s) 18. An example of instrument 40 is described in U.S. Ser. No. 10/300,249, filed Nov. 20, 2002 and entitled "Medical Devices". In addition to the housing 42 and lever 44, the needle biopsy instrument can include a stylet, a cannula and a trigger. The stylet and cannula have portions located within the housing and are configured to be axially movable relatively to each other, between retracted positions and extended positions. The lever is configured to cause the stylet and cannula to move from an extended positions to their retracted or loaded positions. After the stylet and cannula are loaded, the trigger can be used to release the stylet and the cannula to their extended positions. The cannula is generally a hollow sheath, e.g., made of stainless steel, that receives the stylet. The biopsy instrument with its stylet and cannula can be used with other handles described herein. FIG. 5 shows an instrument 50 having a housing 52 and button actuator 54 for operating the instrument. Housing 52 and lever 54 can be formed as generally described for handle 12 having base portion 16 and resilient portion(s) 18. An example of instrument 50 is described in U.S. Ser. No. 10/300,512, filed Nov. 20, 2002 and entitled "Medical Devices".

Figure 6:
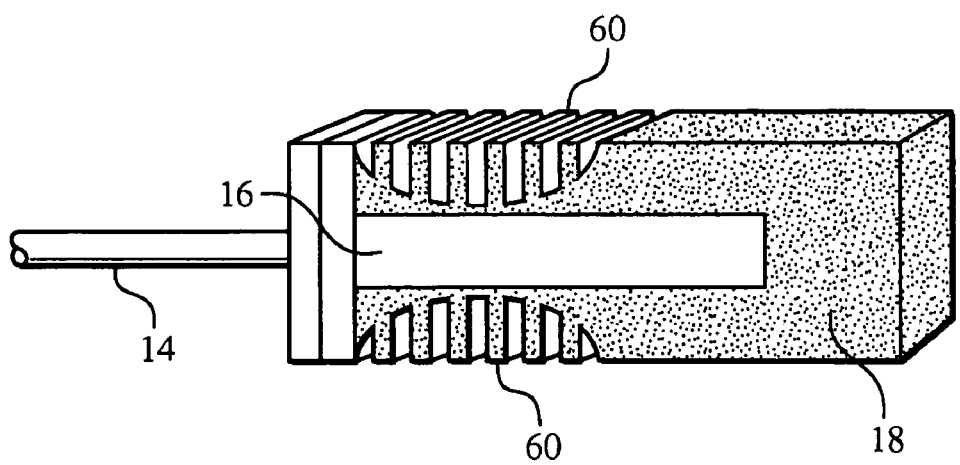
FIG. 6 is a schematic drawing of an embodiment of a handle.

Referring to FIG. 6, in other embodiments, resilient portion(s) 18 can be formed to include flexible elements 60, such as fins or ridges. Elements 60 can enhance the feel of a gripping section and/or absorb shock transferred through the gripping section.

In other embodiments, in addition or alternatively to resilient portion(s) 18, handle 12 or 20 includes one or more portions having texturing, e.g., grooves, scoring, or dimples, to enhance the grip of the handle. The textured portion(s) can include a resilient material or a material of base portion 16, as described above. For example, referring again to FIG. 1A, base portion 16 can be textured.

The handles and gripping sections described above can be used in any medical device where a good grip is desirable, such as those that can get wet during use. Examples of devices include endoscopic devices, ultrasound probes (e.g., Garrison et al., U.S. Pat. No. 6,237,192), or inflation devices for balloon catheters.

All patents, applications, references, and publications referred to above are incorporated by reference in their entirety.

Other embodiments are within the claims.

What is claimed is:

1. A needle biopsy instrument, comprising:
   a cannula;
   a stylet at least partially within the cannula; and
   a handle in which at least a portion of the cannula and stylet are located, the handle having
      a first portion having a first composition,
      a second portion over a selected portion of the first portion, the second portion having a second composition different than the first composition, and
      a third portion over a selected portion of the first portion, the third portion having a third composition different than the first and second compositions.

2. The instrument of claim 1, wherein the handle is generally linear.

3. The instrument of claim 1, wherein the handle is a pistol-like grip.

4. The instrument of claim 1, wherein the handle includes grooves configured to receive a user's finger during use.

5. The instrument of claim 1, wherein the first composition comprises aluminum.

6. The instrument of claim 1, wherein the first composition comprises a polymer.

7. The instrument of claim 1, wherein the first composition includes a material selected from the group consisting of polycarbonate and acrylonitrile-butadiene-styrene.

8. The instrument of claim 1, wherein the first composition is harder than the second composition.

9. The instrument of claim 1, wherein the second composition comprises a polymer.

10. The instrument of claim 1, wherein the second composition comprises a foam.

11. The instrument of claim 1, wherein the second composition comprises a material that results from mixing a foamable, curable polyurethane prepolymer and an aqueous phase containing a latex and a surfactant.

12. The instrument of claim 1, wherein the second composition comprises a urethane.

13. The instrument of claim 1, wherein the second portion defines a flexible ridge.

14. The instrument of claim 1, wherein the second portion defines a plurality of flexible ridges.

15. The instrument of claim 1, wherein the handle has a recess, and the second portion is over the recess.

16. The instrument of claim 1, wherein the handle further comprises an adhesive between the first portion and the second portion.

17. The instrument of claim 1, wherein the second portion interlocks with the first portion.

18. The instrument of claim 1, wherein the second portion contacts a user during use.

19. The instrument of claim 1, wherein the second portion substantially covers the first portion.

20. The instrument of claim 1, wherein the second portion is over more than about 20% of the surface area of the handle.

21. The instrument of claim 1, wherein the second portion is over more than about 40% of the surface area of the handle.

22. The instrument of claim 1, wherein the second composition has a hardness of less than about 100 Shore A.

23. The instrument of claim 1, wherein the third composition comprises a polymer.

24. The instrument of claim 1, wherein the third composition comprises a foam.

25. The instrument of claim 1, wherein the third composition comprises a urethane.

26. The instrument of claim 1, wherein the handle further comprises an adhesive between the first portion and the third portion.

27. The instrument of claim 1, wherein the third portion interlocks with the first portion.

28. The instrument of claim 1, wherein the third portion contacts a user during use.

29. The instrument of claim 1, wherein the third composition has a hardness of less than about 100 Shore A.

* * * * *